United States Patent [19]

Rambacher et al.

[11] 4,113,950

[45] Sep. 12, 1978

[54] PROCESS FOR PREPARING OROTIC ACID AND THIOOROTIC ACID

[75] Inventors: Paul Rambacher, Rosenheim-Mitterfeld; Siegfried Mäke, Kirchdorf, Inn, both of Fed. Rep. of Germany

[73] Assignee: Diamalt Aktiengesellschaft, Munich, Fed. Rep. of Germany

[21] Appl. No.: 831,053

[22] Filed: Sep. 6, 1977

Related U.S. Application Data

[62] Division of Ser. No. 651,145, Jan. 21, 1976, Pat. No. 4,062,847.

[30] Foreign Application Priority Data

Jan. 24, 1975 [DE] Fed. Rep. of Germany ....... 2502951

[51] Int. Cl.$^2$ ................. C07D 239/54; C07D 239/56
[52] U.S. Cl. .................................................. 544/314
[58] Field of Search ........................... 260/251 R, 260

[56] References Cited

U.S. PATENT DOCUMENTS 2,937,175   5/1960   Scriabine .............................. 260/260

FOREIGN PATENT DOCUMENTS 606,804   10/1960   Canada ..................................... 260/260

OTHER PUBLICATIONS

Chemische Fabrik Benckiser, Chem. Abstr., vol. 54 (1960), 8867b.
Moriyama, Chem. Abstr., vol. 59 (1963), 3925.
Chkhivadze et al., Chem. Abstr., vol. 60 (1964), 10679f.

*Primary Examiner*—Paul M. Coughlan, Jr.
*Attorney, Agent, or Firm*—Haseltine, Lake & Waters

[57] ABSTRACT

A method for the preparation of orotic acid and thioorotic acid is described which includes the formation of carboxymethylene-hydantoin or -thiohydantoin and subsequent rearrangement and isolation of orotic acid and thioorotic acid, respectively.

7 Claims, No Drawings

PROCESS FOR PREPARING OROTIC ACID AND THIOOROTIC ACID

This is a division of application Ser. No. 651,145 filed Jan. 21, 1976, U.S. Pat. No. 4,062,847.

The present invention relates to a method of producing orotic or thioorotic acid.

Various methods are already known for producing orotic acid or it s sulfur analog, 2-thioorotic acid. These known methods include the condensation of sodium oxalacetic acid ester with urea or thiourea, said method resulting in relatively low yields of orotic or thioorotic acid, respectively; or the synthesis of the chloromethyl uracyl from chloracetoacetyl chloride (prepared from chlorine and diketene), an urea, and subsequently oxidizing the product thus obtained in the second step with hydrogen peroxide. These and other methods are subject to a number of drawbacks. For example, the difficult handling of the initial materials such as in the case where diketene is used, poor accessibility of the initial materials, or complicated procedures requiring a number of steps with intermediate products requiring isolation, or poor yields are some of the drawbacks.

The condensation of hydantoins and thiohydantoins (imidazolidin-2,4-diones or imidazolidin-2-thiono-4-one compounds, respectively) at the 5- position with carbonyl compounds, which results in 5-alkylidene or aralkylidene- (thio)-hydantoins, respectively, is known from the relevant literature. Reactions with glyoxylic acid, however, have not been described heretofore.

It is an objective of the present invention to provide for a simple and economic method for the preparation of orotic acid or thioorotic acid that is not impaired by the aforementioned shortcomings.

The method according to the present invention for the production of orotic or thioorotic acid is characterized by the fact that hydantoin or thiohydantoin or their $N_1$-acylated derivatives is condensed with glyoxylic acid in alkaline solution to form the salt of the carboxymethylene hydantoin or carboxymethylene thiohydantoin, respectively, said salt is converted with or without isolation, in alkaline solution by means of intramolecular rearrangement into the salt of orotic or thioorotic acid, respectively, and isolating therefrom the free orotic or thioorotic acid by acidification in the manner known pe se.

A modification or variation of the method according to the present invention comprises condensing instead of acylated hydantoin, if need be, acylated hydantoin acid nitrile, if need be, with glyoxylic acid in alkaline solution to form the salt of the carboxymethylene hydantoin acid nitrile, subjecting said resulting salt in alkaline solution to a saponification and cyclization to the carboxymethylene hydantoin, and subsequently converting said compound by intramolecular rearrangement into the salt of the orotic acid, and isolating therefrom the free orotic acid by acidification in the manner known per se.

The reaction in the process or method according to the present invention takes place in alkaline solution and comprises the use of both inorganic and organic bases.

Examples of such bases are the usual inorganic bases such as sodium hydroxide, potassium hydroxide, ammonia, or organic bases such as pyridine and piperidine. The solvent to be used is preferably water because glyoxylic acid is readily soluble in water. However, organic solvents such as lower alcohols may also be used in which glyoxylic acid is sufficiently soluble, for example methanol or ethanol, as well as mixtures of such organic solvents with water.

The pH of the reaction mixture is within the alkaline range, i.e., above 7.0. If acylated hydantoin is used, the pH range of 7.2 to 8.5 will be advantageous. The use of compounds which are not acylated requires maintaining a higher pH of at least 10.

The method according to the present invention is carried out at temperatures within the range of room temperature (18° C.) and reflux temperature of the reaction mixture. Depending on the temperature conditions employed and the reactivity of the hydantoin component, the duration of the reaction varies from about 1 hour to a few hundred hours.

Depending in each case on the adjusted pH of the reaction solution, the employed temperature conditions and the duration of the reaction, it is possible to optionally isolate the intermediate acylated carboxymethylene hydantoin or carboxymethylene thiohydantoin. Said isolation of the intermediate product is more easily accomplished, the less alkaline the reaction medium. For example, with a pH of 7.5, a moderate reaction temperature within the range of from 30° to 50° C. and a long reaction duration of from 100 to 200 hours, the reaction may be carried out only up to the formation of the carbomethylene intermediate products, in which case said products may be isolated in the form of their salts with the use of water as the solvent because said salts are not soluble in the reaction solution. By acidification, for example with hydrochloric acid or sulfuric acid, the free carboxymethylene compounds may be obtained from the salts of the carboxymethylene intermediate products.

The molar ratio of the reaction participants, i.e., glyoxylic acid on the one hand, and hydantoin or thiohydantoin compound, or functional derivatives of hydantoin acid or thiohydantoin acid, respectively, on the other hand amounts preferably to 1:1. However, a molar ratio also of from 2:1 to 1:2 may be used.

The molar ratio of base to glyoxylic acid must at least amount to 1:1 so that a salt of the glyoxylic acid will be obtained. However, said molar ratio is preferably higher than 1:1, for example 1.1:1 up to 10:1, preferably 1.5:1 up to 5:1.

The conversion of the acylated orotic acid or thioorotic acid into free acid when required, takes place by acidifying the reaction mixture, for example with hydrochloric acid or sulfuric acid, whereby the free acids are precipitated. Said free acids may subsequently be separated in a simple manner by filtration and may then be dried. The resulting free acids may be recrystallized, if necessary, from a suitable solvent.

The isolation of the formed salts of the carboxymethylene hydantoin or carboxymethylene thiohydantoin, for example the ammonium, sodium or potassium salt, may be carried out in the above-described manner, however, the method according to the present invention may be carried out particularly advantageously if, in a variation of said method, the further rearrangement to orotic or thioorotic acid is permitted to take place in the same solution or suspension because is was found that such an isolation of the carboxymethylene derivatives is in that case not necessary.

The conversion of the nitrile with glyoxylic acid, in which the nitrogen atom conforming to the 1- position in the hydantoin link may be acylated, if necessary, indicates that the acyclic ureides corresponding to the cyclic hydantoin are capable of condensing with glyoxylic acid with subsequent cyclization.

This reaction also takes place under the conditions specified in the foregoing, i.e., in an alkaline medium.

It was specified above that the hydantoin or thiohydantoin derivatives used as initial compounds, or the hydantoin acid nitrile derivatives may be acylated at the nitrogen atom present in the 1- position. The acyl radical generally comprises from 2 to 10 carbon atoms, advantageously from 2 to 4 carbon atoms, while it is preferably the acetyl radical.

The reactions taking place in the method according to the present invention are shown in the following reaction diagram:

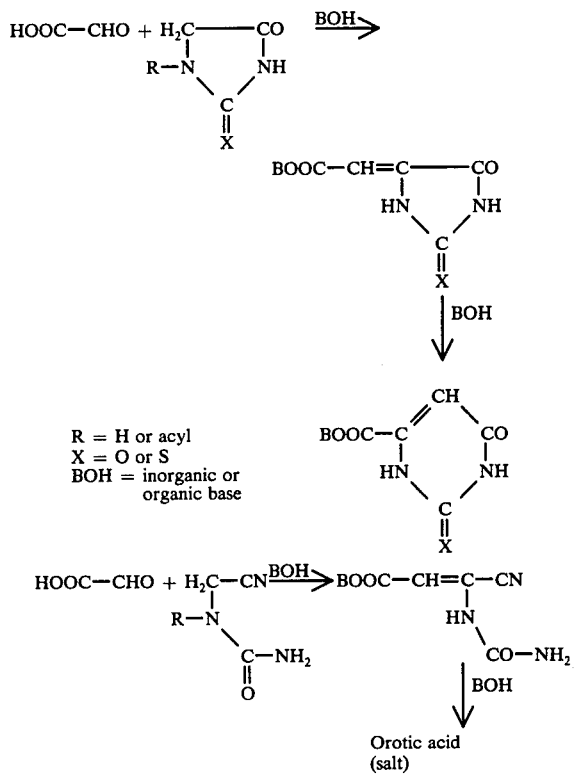

R = H or acyl
X = O or S
BOH = inorganic or organic base

The affinity with respect to the glyoxylic acid decreases in the sequence acetylthiohydantoin > thiohydantoin > acetylhydantoin > -hydantoin acid nitrile > hydantoin. The reaction conditions are selected accordingly.

The initial materials of the method according to the present invention, namely glyoxylic acid, hydantoin, thiohydantoin or hydantoinic acid nitrile, are compounds which are commercially available or readily accessible.

The present invention is explained in greater detail with the help of the following examples. Glyoxylic acid is understood to be glyoxylic acid monohydrate in all examples.

EXAMPLE 1

4.6 Grams of glyoxylic acid (0.05 mol) and 7.9 grams acetylthiohydantoin (0.05 mol) were added to a solution of 15 ml piperidine (0.15 mol) in 50 ml water. The mixture was stirred for 1 hour at room temperature, subsequently boiled for 2 hours under reflux, subsequently permitted to cool slightly and then admixed with 60 ml water and concentrated hydrochloric acid in an amount sufficient to render the suspension strongly acidic. The precipitated thioorotic acid was isolated and dried. 7.5 Grams thioorotic acid were obtained which corresponds to 87.3% of the theoretical yield. The identity of the thioorotic acid was confirmed by IR-spectrum.

EXAMPLE 2

2.7 Grams glyoxylic acid and 3.7 grams thiohydantoin were dissolved in a solution 8.5 ml piperidine in 30 ml water. The mixture was stirred for 1 hour at room temperature, boiled for 2 hours under reflux, whereupon 40 ml water were added and acidification was carried out with hydrochloric acid up to a pH of 2. 3.6 Grams of thioorotic acid were obtained corresponding to 73% of theory.

EXAMPLE 3

To a mixture of 4.6 grams glyoxylic acid and 7.9 grams acetylthiohydantoin in 50 ml water was added under agitation about 15 ml of 8N soda lye, whereby a pH of 8.5 is adjusted which by further addition of lye in small amounts during the next 3 hours under agitation was maintained at room temperature. This was followed, upon addition of 40 ml 2n NaOH by further boiling under reflux for 2 hours. After treatment with active carbon, precipitation was carried out by addition of hydrochloric acid up until the reaction mixture became acidic. 5.4 Grams thioorotic acid were obtained, corresponding to 63% of the theoretical yield.

EXAMPLE 4

A solution of 4.6 grams glyoxylic acid and 7.1 grams acetylhydantoin in 50 ml water was brought to a pH of 7.5 by adding 8N soda lye and agitated under controlled pH for a duration of 160 hours at 40° C. 6.3 Grams of the sodium salt of the carboxymethylene hydantoin were precipitated during said time. By acidification with hydrochloric acid there were obtained 4.5 grams carboxymethylene hydantoin corresponding to 57.7% of the theoretical yield.

EXAMPLE 5

To a solution of 9.2 grams glyoxylic acid and 10 grams hydantoin in 75 ml water under reflux conditions was added, dropwise, 50 ml 8N soda lye over a 15 minute period, followed by further refluxing for 1 hour and precipitation of the sodium salt of the orotic acid by the addition of hydrochloric acid to a pH of 6. 8.5 Grams Na-orotate were obtained, corresponding to 49% of theory.

EXAMPLE 6

To a solution of 5 grams hydantoinic acid nitrile and 4.6 grams glyoxylic acid in 200 ml water was added, dropwise, 62.5 ml 8N soda lye over a 1 hour period at 65° C. The mixture was subsequently stirred for 2 additional hours at said temperature. The pH was adjusted to 6 by means of concentrated hydrochloric acid, and 5.7 grams sodium orotate were obtained, corresponding to 64% of theory.

We claim:
1. A process for preparing a compound of the formula wherein X is oxygen or sulfur which comprises reacting a compound of the formula:

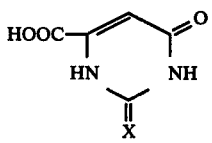

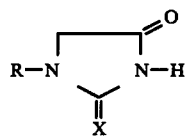

wherein R is hydrogen or an acyl group and X is as defined above, with glyoxylic acid in an alkaline medium to form a carboxymethylene intermediate of the formula:

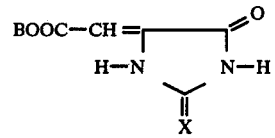

wherein B is an inorganic or organic cation resulting from the alkaline medium and X is as defined above, converting said compound, in an alkaline medium into the salts of a compound of Formula I, above, and recovering the free acid.

2. The process according to claim 1 wherein the reaction to form the carboxymethylene intermediate is carried out at a pH of from 7.5 to 11.

3. The process according to claim 1, wherein the reaction comprising isolation of the carboxymethylene intermediate is isolated at a pH of from 7.2 to 7.8 before conversion to the free acid.

4. The process according to claim 1 wherein the proportion of base to glyoxylic acid is in the molar ratio of from 1.5:1 to 5:1.

5. The process according to claim 1 wherein a solvent is used and said solvent is water or a mixture comprising water and $C_1$-$C_2$-alkanol.

6. The process according to claim 1 wherein the base used is NaOH, KOH, $NH_3$, pyridine or piperidine.

7. The process according to claim 1 wherein the reaction to form the carboxymethylene intermediate is carried out at a temperature between 18° C. and the reflux temperature of the reaction mixture.

* * * * *